United States Patent [19]

Sanghvi et al.

[11] Patent Number: 4,664,121

[45] **Date of Patent: * May 12, 1987**

[54] INTRAOPERATIVE SCANNER

[75] Inventors: Narendra T. Sanghvi; Francis J. Fry; Richard F. Morris; Richard A. Stuber, all of Indianapolis, Ind.

[73] Assignee: Indianapolis Center for Advanced Research, Indianapolis, Ind.

[ * ] Notice: The portion of the term of this patent subsequent to Feb. 25, 2003 has been disclaimed.

[21] Appl. No.: 785,483

[22] Filed: Oct. 8, 1985

Related U.S. Application Data

[63] Continuation-in-part of Ser. No. 600,095, Apr. 13, 1984, Pat. No. 4,572,200.

[51] Int. Cl.[4] .............................................. A61B 10/00

[52] U.S. Cl. ....................................... 128/660; 73/634

[58] Field of Search ................................ 128/660–663; 73/618–620, 633, 634

[56] References Cited

U.S. PATENT DOCUMENTS

| | | | |
|---|---|---|---|
| 3,269,173 | 8/1966 | Von Ardenne . | |
| 4,059,098 | 11/1977 | Murdock . | |
| 4,092,867 | 6/1978 | Matzuk | 128/660 |
| 4,120,291 | 10/1978 | Paton et al. | 73/618 |
| 4,257,272 | 3/1981 | Sloman | 73/633 |
| 4,321,600 | 3/1982 | Blaser . | |
| 4,398,425 | 8/1983 | Matzuk | 73/633 |
| 4,399,703 | 8/1983 | Matzuk | 128/660 |
| 4,418,698 | 12/1983 | Dory | 128/660 |
| 4,421,118 | 12/1983 | Dow et al. | 128/660 |
| 4,433,691 | 2/1984 | Bickman | 128/660 |
| 4,479,388 | 10/1984 | Matzuk | 73/634 |

FOREIGN PATENT DOCUMENTS 0089131 9/1983 European Pat. Off. .

OTHER PUBLICATIONS

Hewlett Packard 28 mm Diameter Two Channel Incremental Optical Encoder Kit Heds-5000 Series.

*Primary Examiner*—Kyle L. Howell
*Assistant Examiner*—Ruth S. Smith
*Attorney, Agent, or Firm*—Barnes & Thornburg

[57] ABSTRACT

A heat-sterilizable ultrasonic surgical scanner includes an ultrasonic transducer and a permanent magnet motor for moving the transducer along an arcuate path. The scanner further includes a housing for the ultrasonic transducer and the motor. The housing includes an acoustically transparent window for transmitting ultrasonic energy from and into the housing. A resilient diaphragm permits expension and contraction of a coupling fluid with which the housing is filled without causing fluid loss from the housing due to leakage. The resilient diaphragm is mounted at a location remote from the acoustically transparent window.

12 Claims, 10 Drawing Figures

FIG. 1
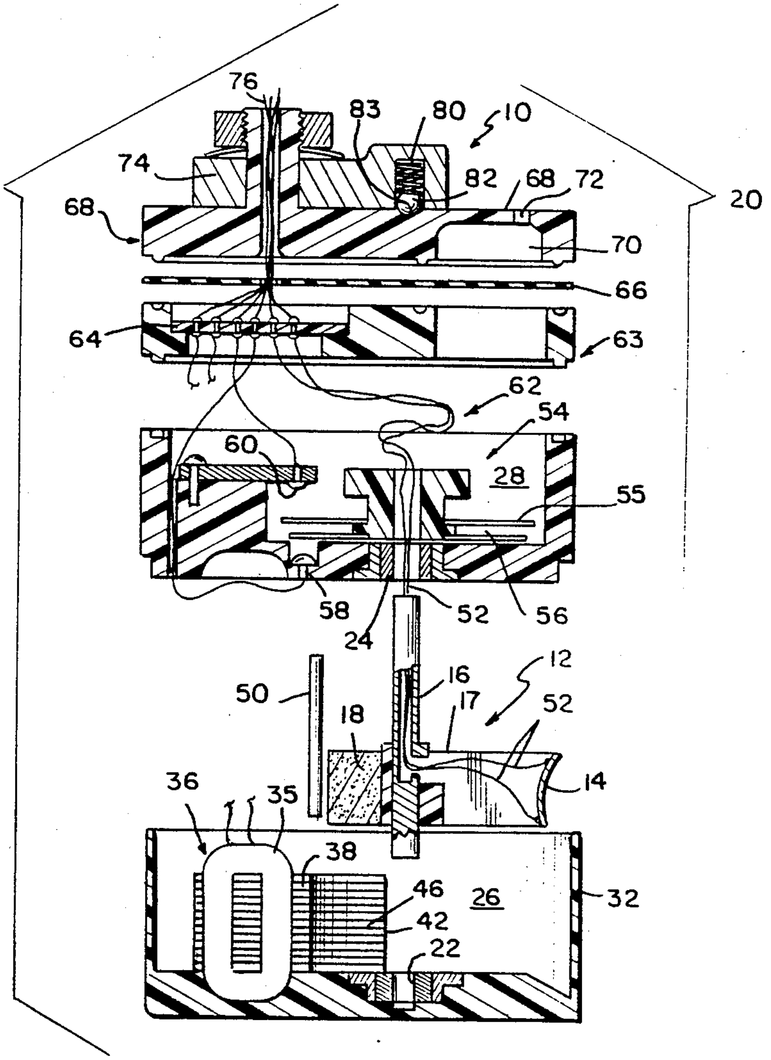
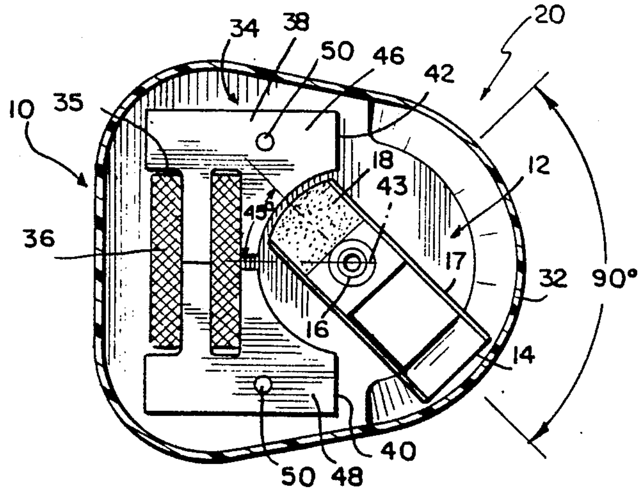
FIG. 2

INTRAOPERATIVE SCANNER

This a continuation-in-part of copending U.S. Ser. No. 600,095, filed April 13, 1984 now U.S. Pat. 4,572,200 and assigned to the same assignee as this application.

This invention relates to ultrasound sector scanning apparatus, and more particularly to ultrasound sector scanning systems that utilize transducers mounted for movement within predetermined paths and mounted for use during surgery.

The use of ultrasonics in a variety of testing situations has been widespread and includes the medical diagnostic and therapeutic fields. In a medical B-scan, transducers have been utilized to move along a linear path with transverse oscillation or rocking in acoustically coupled relationship with a patient to provide a "sector scan." All of the scanners heretofore used for sector scanning have been for external use only. There is a continuing need for ultrasonic imaging equipment that can be utilized in open-body surgical procedures. There are several ultrasonic scanner designs available. However, none have found wide acceptance in the operating room environment. There are a number of factors believed responsible for this lack of acceptance: (1) most of these scanners are far too large for use in an opening produced during a surgical procedure; (2) the majority of the scanners are not autoclavable, that is, not capable of withstanding the high temperatures utilized during sterilization which is required for repeated use of the scanner in such surgical procedures; (3) some of the scanners do not have sufficient accuracy in the controlling of the transverse oscillation or "wobble" during a scan; (4) the majority of such scanners have an insufficient field of view from which the transducer acoustical signal is directed; and (5) the transducers that are now available lack the reliability necessary to be trusted in an operating room environment where open body surgical scanning is necessitated.

It is therefore an object of the present invention to provide an ultrasound sector scanner system for use in open body surgical procedures.

It is another object of the present invention to provide an ultrasound sector scanner system that is capable of withstanding high temperature sterilization to permit repeated use of the scanner in open body surgical procedures.

It is yet another object of the present invention to provide an ultrasonic sector scanner that is sufficiently reliable that it can be utilized in an operating room environment.

An ultrasound sector scanner system in accordance with the present invention includes a motor rotor assembly that includes an ultrasonic transducer mounted on a hollow shaft by means of an ultrasonic damping material. A small, high coercive force permanent magnet is also mounted on the hollow shaft. Flexible lead wires are coupled to the transducer and pass through the hollow shaft. The magnetic axis of the permanent magnet is aligned such that it passes through the transducer. The rotor assembly is mounted in a housing assembly which is constructed of a series of interconnecting chambers which are sealable to prevent leakage of coupling fluid utilized in the housing. The housing assembly includes a first housing component providing a window through which the ultrasonic energy is coupled. The first housing component also includes a cavity for housing a stator assembly. The motor stator includes windings and a magnetic core of transformer-type laminations. The laminations are constructed so as to have magnetic poles at about ±45° of rotation of the rotor, to permit free rotation of said rotor within the 45° range. By energizing the windings with current of a first polarity and then current of a second polarity, the rotor is caused to rotate approximately ± 45° about the center of the window. Reversing the polarity of current through the windings oscillates the rotor in an arc about a center position, thus providing the desired sector scanning of the subject of interest. The rotation of the rotor may be limited by end stops built into the poles to provide viscous damping to aid in maintaining the ±45° limits of rotation of the rotor.

A second housing component provides a bearing for the shaft. In one embodiment of the invention, this component also houses a digital rotor position transducer. The rotor position transducer is mounted on a portion of the shaft which extends into the second housing portion.

A digital transducer according to one aspect of the present invention uses a two-track optical encoder, with the first track being provided by a disk which is opaque over most of its area with a clear area only within the 90° angular sector (±45°) to be scanned. A system including a photoemitter on one side of the disk and a photoreceptor on the other side of the disk detects the change in opacity as the disk rotates with the shaft. Conventional circuitry (for example, an edge-triggered bistable circuit, not shown) reverses the current to the windings of the stator, thus reversing the rotation of the rotor with minimal overshoot. Upon re-illuminating of the photodetector, the position of the rotor is again obtained.

The second track of the encoder is provided with a number of equally spaced clear and opaque sections defining equal increments of rotation. Thus, with a known starting point, the position of the rotor at any instant can be determined to a high degree of accuracy and reliability. To eliminate the problems of leakage, the encoder is operated submerged in the ultrasonic coupling fluid within the housing. One housing section includes a feed-through bulkhead with molded-in electrical conductors. Contact can be made to the conductors from the motor stator, encoder, and transducer without leakage through the bulkhead's molded-in conductors. The bulkhead also serves as one retaining wall for a diaphragm formed from a high-temperature flexible material, such as a silicone, that permits expansion and contraction of the coupling fluid during operation and sterilization.

According to another embodiment of the invention, the encoder disk remains in place on the motor shaft but the light source and photodetector are disconnected. In this emobodiment, the encoder disk is thought to function as a flywheel/brake. The coupling fluid interacts with code slots in the disk to make the rotor motion highly predictable. In this embodiment, a memory associated with the ultrasound display is written to during the scan of the rotor in one direction only. Information which is returned to the transducer during the scan in the other direction, the "retrace" of the rotor, is discarded. This is done in this embodiment because the position of the rotor is known with sufficient precision at one point during the input waveform to the stator, that point being essentially at the beginning of the scan interval. If the retrace information is written, it has been found that alternating the scan and retrace field echo information does not provide a sufficiently precise ultrasound image.

In this embodiment of the invention, the encoder disk is modified slightly. The disk is a 28 mm diameter disk. Thus its circumference is approximately 88 mm. A 4–5 mm long peripheral section at each end of a 90° sector of the disk is removed to the depth of the code slots. This disk thus modified serves the flywheel/brake function in this embodiment.

According to another embodiment of the invention, the encoder disk and the lamp and photodetector are all removed from the scanner housing. As in the embodiment just discussed, the memory associated with the ultrasound display is written to only during the scan of the rotor in a first direction. The rotor's retrace in the opposite direction is blanked since the rotor's position is only known with the degree of accuracy necessary to generate a visual display at the point at which the scan in the first direction begins. This point is known because it coincides in time with a high degree of predictability with a point on the input waveform to the stator.

Features and advantages of the invention will become apparent to those skilled in the art upon consideration of the following detailed descriptions of embodiments exemplifying the best mode of carrying out the invention as presently perceived. The detailed descriptions particularly refer to the accompanying figures in which:

FIG. 1 illustrates an exploded cross-sectional view of an ultrasound sector scanner according to a first embodiment of the present invention;

FIG. 1*a* illustrates a sectional view of the assembled ultrasound sector scanner system of FIG. 1 showing expansion of a coupling fluid during exposure to heat;

FIG. 2 illustrates a sectional view of the system of FIG. 1*a* taken generally along section lines 2—2 thereof;

Figure 1A:
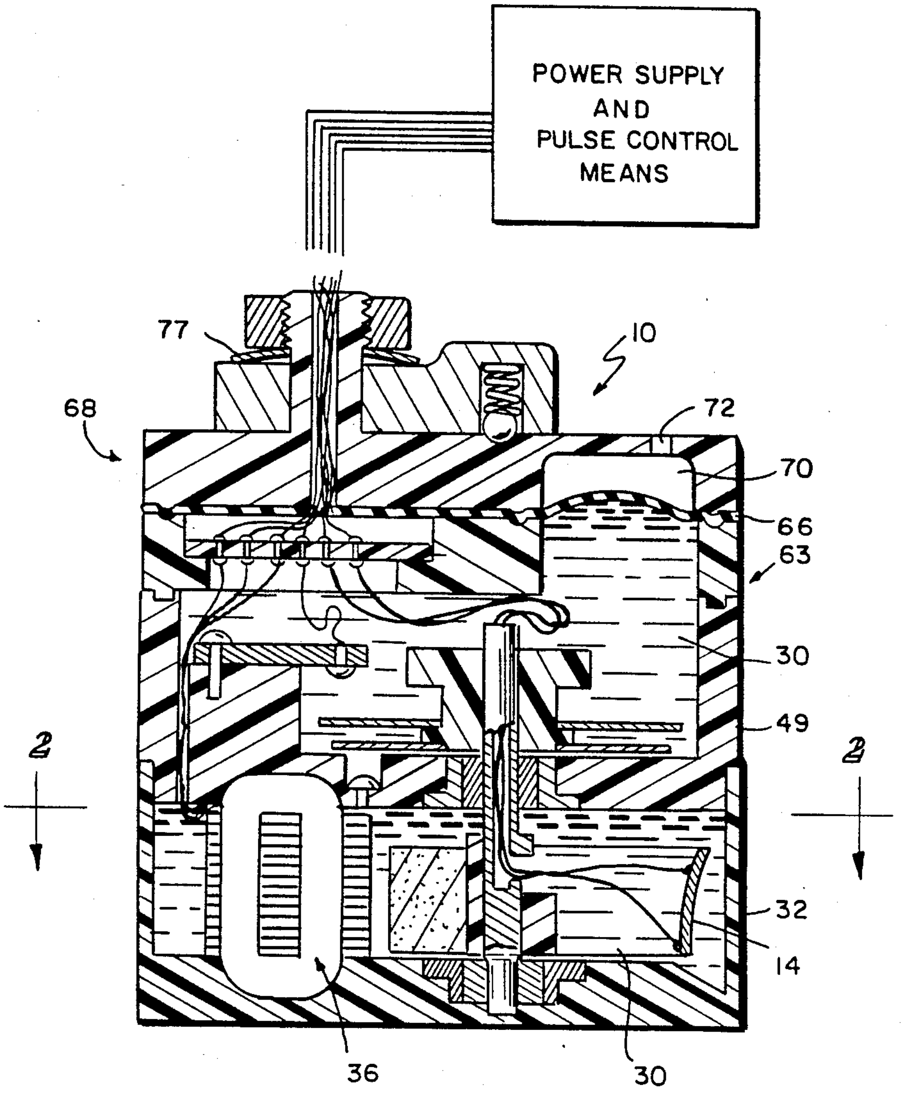

Referring to FIG. 1, an ultrasound sector scanner system 10 includes a rotor assembly 12. The rotor assembly 12 is made up of an ultrasonic transducer 14 that is attached to a hollow shaft 16 by an ultrasonic damping material 17, such as Teflon-loaded epoxy. A small, high coercive force permanent magnet 18 is also attached to the shaft 16 by ultrasonic damping material. The rotor assembly 12 is mounted for rotation within a housing 20 in bearings 22 and 24. The bearings 22 and 24 permit easy rotation of the shaft 16 within the housing 20, while precluding axial motion of the shaft 16 within the housing 20. The housing 20 is constructed to include a series of interconnecting chambers including the chamber 26 housing the transducer and a chamber 28 housing an encoder. These interconnecting chambers are sealed, as will be discussed, to prevent leakage of the coupling fluid 30 that is utilized within the transducer housing 26.

The transducer chamber 26 includes a window 32 through which ultrasonic energy is coupled. This window 32 is molded into, and forms a part of, the housing 20 which is formed from a high temperature plastic (e.g. UDEL P1700, available from Union Carbide Company). By forming the window integrally with the housing, the possibility of leakage from the window during use or sterilization is greatly reduced.

The transducer chamber 26 is suitably configured to accommodate a stator assembly 34. The stator assembly 34 includes windings 36 which are machine-wound on a bobbin 35, and a magnetic core 38 constructed from transformer-type laminations or a high-permeability ferrite. The magnetic poles 40 and 42 of the core 38 are located at about ±45° of rotation of the rotor 12 in either direction from the center 43 of the window 32.

The poles 40 and 42 permit free rotation of rotor 12 between the ± 45° positions. By energizing the coil 36 of the stator 34 with current of a first polarity, a magnetic field is established that causes the rotor 12 to move toward a position rotated approximately 45° from the center 43 of the window 32 (see FIG. 2). By reversing the current, the rotor 12 will tend to move approximately 90° to a point approximately 45° on the other side of center 43 of the window 32. By alternately reversing the polarity of current through the coils 36 of the stator 34, the rotor 12 can be made to oscillate in an approximately 90° arc about the center 43 of the window 32, thus defining a sector of the tissue of interest for scanning by the ultrasonic transducer 14.

The core 38 is configured with legs 46 and 48, the distal ends of which extend generally to the ± 45° positions of rotor 12 rotation to provide the poles 40 and 42, respectively. The pole 40 and 42 faces are themselves contoured in a somewhat concave manner to conform to the transverse sectional configuration of the rotor 12. The fluid coupling medium with which cavity 26 is filled coacts with the pole 40 and 42 faces and rotor 12 to act as a snubber or shock absorber for the rotor at the endpoints of its ± 45° traversals of the window 32. This promotes a smooth, shock-free deceleration of the rotor 12 near these endpoints.

Lamination locator pins 50 locate the stator 34 lamination position accurately and prevent movement of the stator assembly 34. Alternatively, the dimensions of the cavity can be such as to prevent movement of the stator assembly 34. Flexible conductors 52 with high temperature insulation, such as Teflon, are attached to the ultrasonic transducer 14 and pass through the hollow shaft 16 and the bearing 24 into chamber 28. The magnetic axis of the permanent magnet 18 is aligned so as to pass through the transducer 14. The sonic axis of the transducer 14 can be perpendicular to the axis of the shaft 16 or may be offset by, for example, 15° to reduce reflections from the window 32.

The transducer housing portion 49 which provides chamber 28, also houses a shaft position transducer 54 including an encoder 56. Any of a variety of encoders, such as optical encoders, magnetic encoders, and contact encoders, can be utilized. In the preferred embodiment, a two track optical encoder 56 is used. One track of disk 55 of the encoder is opaque over most of its area, with a clear area only within the 90° sector to be scanned. The second track of disk 55 of the optical encoder 56 is provided with a plurality of equally spaced clear and opaque sections defining equal increments of rotation (for instance, 125 pairs of clear and opaque sections for 90° rotation, to define at least every 0.72° of rotation).

A photoemitter 58 is located on one side of the disk, and a photodetector 60 on the other side of the disk detects the changes in transmittance as the disk 55 rotates with the shaft 16. In use, conventional circuitry, such as an edge triggered bistable circuit (not shown), responds to certain of these changes in transmittance and reverses the current to the windings 36 of the stator 34 and thus reverses the rotation of the rotor 12. The photodetector 60 will be re-illuminated following slight rotation of the rotor 12 back in the reverse direction and the position of the rotor 12 can be ascertained. By knowing the starting point of rotation and the increments of rotation from that point, the position of the rotor 12 at any time can be determined with a high degree of accuracy and reliability. By using this shaft position transducer 54 utilizing a two track optical encoder, the transducer 14 position can be reliably determined.

To couple the transducer 14 output at maximum amplitude through window 32, and to couple reflections at maximum amplitude returning through window 32 back to transducer 14, cavity 26 is filled with a coupling fluid. To eliminate any problems of leakage of the coupling fluid, the encoder 56 is operated immersed in the coupling fluid. Degradation of the photoemitter 58 and photodetector 60 is prevented by using high temperature hermetically sealed units with built-in lenses. Suitable units are available from Texas Instruments (the TIL-23 Series and the TIL-601 Series). The encoder disk 55 is preferably constructed using photoetching techniques in metal for low inertia and high temperature resistance.

The conductors 52 pass through the hollow shaft 16 and through the center of the encoder 56. These conductors are then wound in a loose "clock spring" coil 62 and positioned in the encoder housing cavity 28. Stresses on the conductors 52 caused by the oscillation of the transducer 14 are thus distributed over a considerable length, leading to long flex life of the conductors 52.

The chamber 28 is closed by a housing portion 63 including a feed-through bulkhead 64 through which conductors from the stator assembly 34, transducer 54, and transducer 14 are coupled by conductive terminations molded into the bulkhead, while maintaining the sealed integrity of chamber 26 and chamber 28. The housing portion 63 serves as one of the retaining walls for a resilient diaphragm 66. The diaphragm 66 is clamped between the housing portion 63 and a handle support portion 68. The diaphragm 66 permits expansion and contraction of the coupling fluid in chambers 26 and 28 during use and sterilization of the system following use. The diaphragm 66 is preferably made from a high temperature flexible material, such as a silicone. Alternatively, diaphragm 66 can be a metal bellows. The handle support portion 68 of housing 20 defines with diaphragm 66 an expansion chamber 70 which is provided with one or more vents 72 for ventilation of the interior of the chamber 70 to the exterior. The expansion chamber 70 protects the diaphragm 66 during use and sterilization.

The handle support portion 68 is provided with a shaft extension 76 which mounts a handle assembly 74. Shaft extension 76 is hollow to permit the conductors 52 to pass from the housing 20 to external circuity (not shown). To prevent stress to the bulkhead connections, the conductors 52 can be glued into the shaft extension 76 using a suitable high temperature adhesive. The handle assembly 74 is pivotable about shaft extension 76. Handle assembly 74 is mounted to shaft extension 76 by sliding the shaft 76 into an opening provided on handle assembly 74, slipping a Belville washer 77 onto shaft 76 and threading a nut 78 onto the end of shaft 76, capturing the handle assembly and Belville washer on shaft 76. A spring 80-urged detent ball 82 cooperates with detent positions 83 (only one of which is shown) on the housing portion 68 to permit locking of the handle assembly 74 in various rotational orientations with respect to housing portion 68.

The coupling fluid that fills chambers 26, 28 and 63 is preferably a light grade of mineral oil. Mineral oil provides a good compromise between sonic velocity, temperature resistance, clarity, lubrication of the bearings 22 and 24, and inertness with respect to other materials to which it is exposed in chambers 26 and 28.

The system 10 thus provides an ultrasonic scanner that is accurate, can be hand-manipulated for insertion into a surgical cavity, and which is durable enough to withstand sterilization temperatures.

Figure 3:
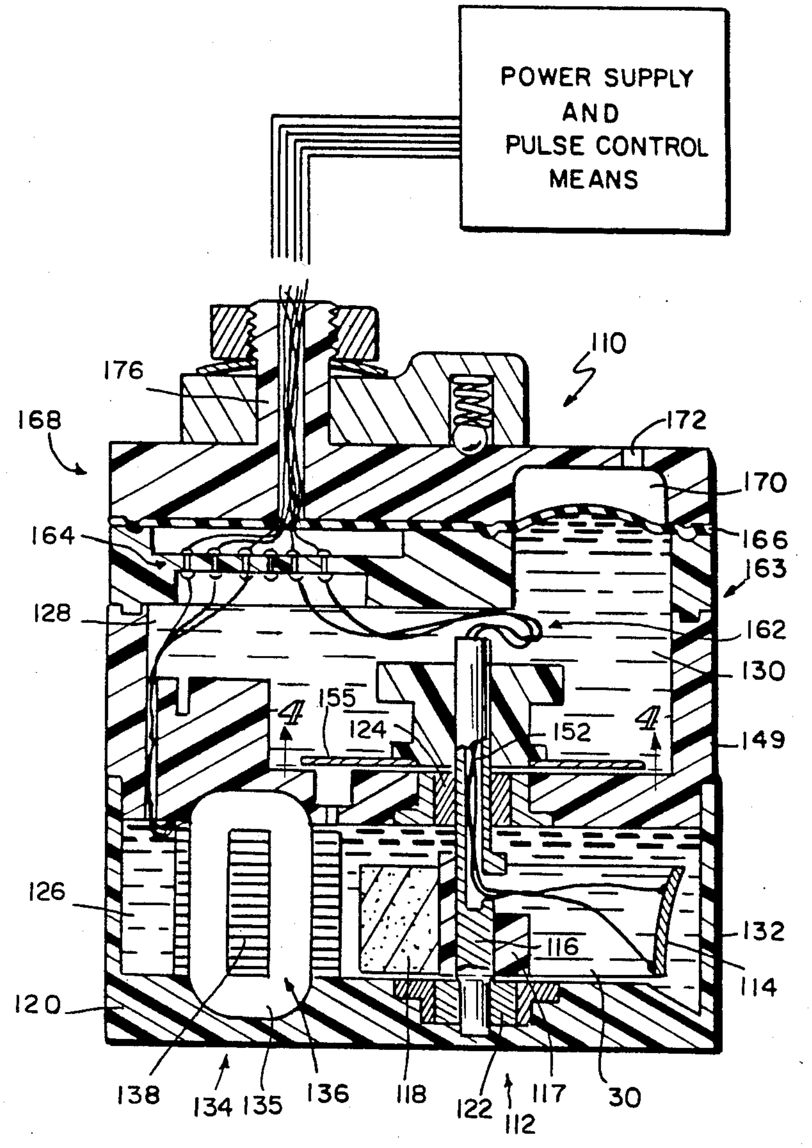
FIG. 3 illustrates a cross sectional view of an ultrasound sector scanner according to a second embodiment of the present invention.
Figure 4:
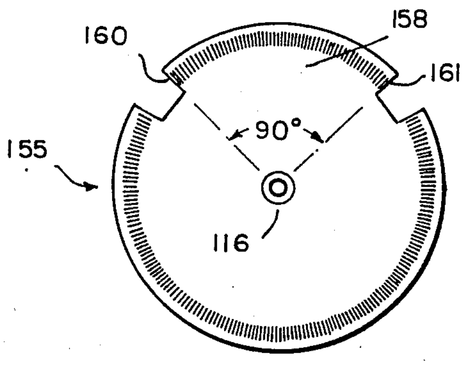
FIG. 4 illustrates a sectional view of a detail of the embodiment of FIG. 3 taken generally along section lines 4—4 of FIG. 3.

Referring to FIGS. 3–4, an ultrasound sector scanner system 110 includes a rotor assembly 112. The rotor assembly 112 is made up of an ultrasonic transducer 114 that is attached to a hollow shaft 116 by an ultrasonic damping material 117, such as Teflon-loaded epoxy. A small, high coercive force permanent magnet 118 is also attached to the shaft 116 by ultrasonic damping material. The rotor assembly 112 is mounted for rotation within a housing 120 in bearings 122 and 124. The bearings 122 and 124 permit easy rotation of the shaft 116 within the housing 120, while precluding axial motion of the shaft 116 within the housing 120. The housing 120 is constructed to include a series of interconnecting chambers including the chamber 126 housing the transducer and a chamber 128. These interconnecting chambers are sealed to prevent leakage of the coupling fluid 130 that is utilized within the transducer housing 126.

The transducer chamber 126 includes a window 132 through which untrasonic energy is coupled. Window 132 is molded into, and forms a part of, the housing 120 which, again, is illustratively constructed from Union Carbide UDEL P1700.

The transducer chamber 126 is suitably configured to accommodate a stator assembly 134. The stator assembly 134 includes windings 136 which are machine wound on a bobbin 135, and a magnetic core 138 constructed from transformer type laminations or a high permeability ferrite. The magnetic poles (not shown) of the core 138 are similar to the poles 40, 42 of FIG. 1 and are located at about ±45° of rotation of the rotor 112 in either direction from the center of the window 132.

The poles permit free rotation of rotor 112 between the ±45° positions. By energizing the coil 136 of the stator 134 with current of a first polarity, a magnetic field is established that causes the rotor 112 to move toward a position rotated approximately 45° from the center 143 of the window 132. By reversing the current, rotor 112 will tend to move approximately 90° to a point approximately 45° on the other side of the center of the window 132. By alternately reversing the polarity of current through the coils 136 of the stator 134, the rotor 112 can be made to oscillate in an approximately 90° arc about the center of the window 132, thus defining a sector of the tissue of interest for scanning by the ultrasonic transducer 114.

The core 138 is configured with legs (not shown) similar to legs 46 and 48 of FIG. 1, the distal ends of which extend generally to the ±45° positions of rotor 112 rotation to provide the poles. The fluid coupling medium with which cavity 126 is filled coacts with the pole faces and rotor 112 to act as a snubber or shock absorber for the rotor at the endpoints of its 45° traversals of the window 132. This promotes a smooth, shock free deceleration of the rotor 112 near these endpoints.

Lamination locator pins (not shown) locate the stator 134 lamination position accurately and prevent movement of the stator assembly 134. Alternatively, the dimensions of the cavity can be such as to prevent movement of the stator assembly 134. Flexible conductors 152 with high temperature Teflon insulation are attached to the ultrasonic transducer 114 and pass through the hollow shaft 116 and the bearing 124 into chamber 128. The magnetic axis of the permanent magnet 118 is aligned so as to pass through the transducer 114. The sonic axis of the transducer 114 can be perpendicular to the axis of the shaft 116 or may be offset by, for example, 15° to reduce reflections from the window 132.

The transducer housing portion 149 which provides chamber 128, also houses the disk 155 of a shaft position transducer.

As can best be seen in FIG. 4, the disk 155 is a circular metal disk on the shaft 116 of the scanner. The illustrative disk 155 has a diameter of approximately 28 mm and thus a circumference of approximately 88 mm. It is slotted approximately every 0.72° around its periphery. The slots are illustratively formed by chemically etching through the metal disk 155. A region 158 having an angular dimension of 90° is bounded by two sectors 160, 161, from which the material of the disk 155 has been removed to the radial depth of the slots by any suitable technique. Each sector 160, 161 extends for about 4–5 mm around the periphery of the disk 155. When a scanner constructed according to FIGS. 1, 1*a* and 2 but having the configuration of disk 155 was constructed, it was determined that the encoder output waveform resembled the waveform of FIG. 5. From this waveform it was determined that a scanner could be constructed which did not rely on a position encoder for feedback of transducer 114 position. This conclusion was reached because of the regularity of the starting point of the waveform from the encoder and the predictability of the coincidence of a certain point on the waveform with a certain point on the drive current waveform to the motor coil 36 of FIGS. 1. 1*a* and 2 and 136 of FIG. 3.

To couple the transducer 114 output at maximum amplitude through window 132, and to couple reflections at maximum amplitude returning through window 132 back to transducer 114, cavity 126 is filled with a coupling fluid.

The motor coil 136 conductors 152 pass through the hollow shaft 116. These conductors are then wound in a loose "clock spring" coil 162 and positioned in the motor housing cavity 128. Stresses on the conductors 152 caused by the oscillation of the transducer 114 are thus distributed over a considerable length, leading to long flex life of the conductors 152.

The chamber 128 is closed by a housing portion 163 including a feed through bulkhead 164 through which conductors 152 from the stator assembly 134 and transducer 114 are coupled by conductive terminations molded into the bulkhead, while maintaining the sealed integrity of chamber 126 and chamber 128. The housing portion 163 serves as one of the retaining walls for a resilient diaphragm 166. The diaphragm 166 is clamped between the housing portion 163 and a handle support portion 168. The diaphragm 166 permits expansion and contraction of the coupling fluid in chambers 126 and 128 during use and sterilization of the system following use. The diaphragm 166 is preferably made from a high temperature flexible material, such as a silicone Alternatively, diaphragm 166 can be a metal bellows. The handle support portion 168 of housing 120 defines with diaphragm 166 an expansion chamber 170 which is provided with one or more vents 172 for ventilation of the interior of the chamber 170 to the exterior. The expansion chamber 170 protects the diaphragm 166 during use and sterilization.

The handle support portion 168 is provided with a shaft extension 176 which mounts a handle assembly (not shown). Shaft extension 176 is hollow to permit the conductors 152 to pass from the housing 120 to external circuitry, in FIGS. 7–8. To prevent stress to the bulkhead connections, the conductors 152 can be glued into the shaft extension 176 using a suitable high-temperature adhesive. The handle assembly can be like handle assembly 74 shown in FIG. 1. The coupling fluid that fills chambers 126, 128 and 163 is preferably a light grade of mineral oil. The system 110 thus provides an ultrasonic scanner that is accurate, can be hand manipulated for insertion into a surgical cavity, and which is durable enough to withstand sterilization temperatures.

Figure 6:
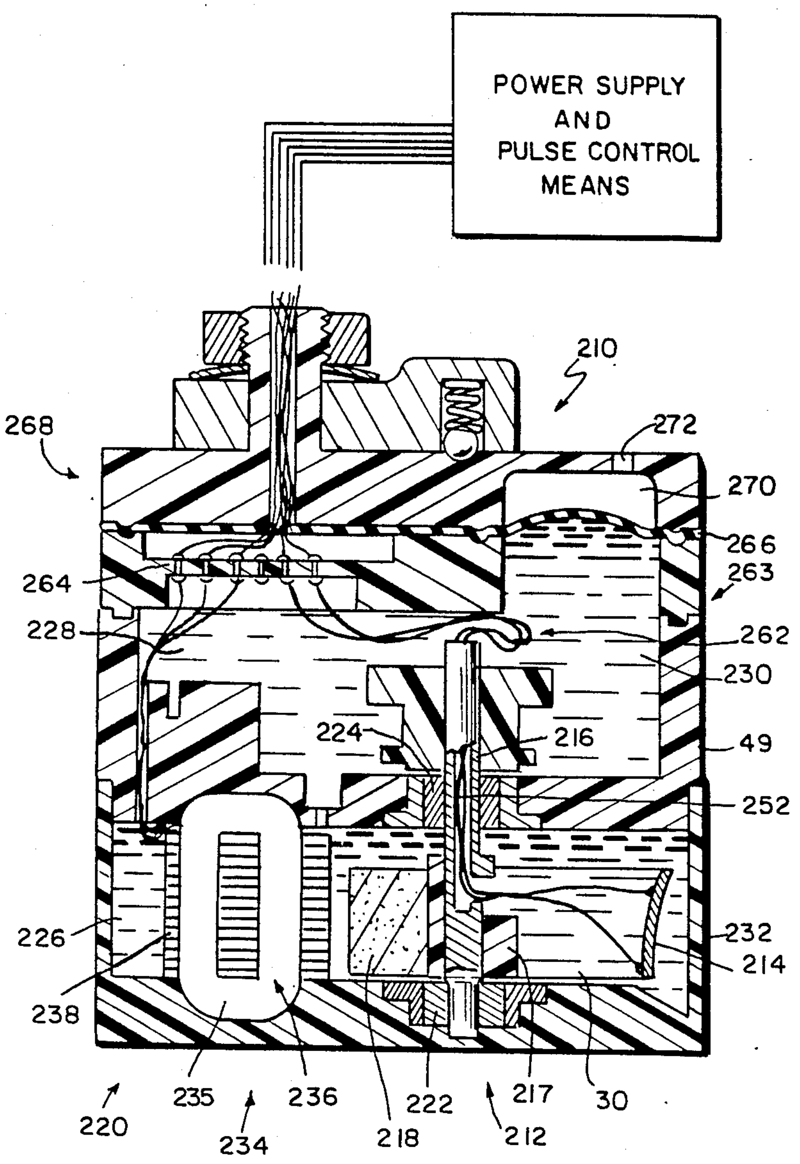
FIG. 6 illustrates a sectional view of an ultrasound sector scanner according to a third embodiment of the present invention.

Referring to FIG. 6, an ultrasound sector scanner system 210 includes a rotor assembly 212. The rotor assembly 212 is made up of an ultrasonic transducer 214 that is attached to a hollow shaft 216 by an ultrasonic damping material 217, such as Teflon-loaded epoxy. A small, high coercive force permanent magnet 218 is also attached to the shaft 216 by ultrasonic damping material. The rotor assembly 212 is mounted for rotation within a housing 220 in bearings 222 and 224. The bearings 222 and 224 permit easy rotation of the shaft 216 within the housing 220, while precluding axial motion of the shaft 216 within the housing 220. The housing 220 is constructed to include a chamber 226 housing the transducer and chamber 228. Chambers 226, 228 are sealed to prevent leakage of the coupling fluid 230 that is utilized within chambers 226, 228.

The transducer chamber 226 includes a window 232 through which ultrasonic energy is coupled. This window 232 is molded into, and forms a part of, the housing 220 which is formed from Union Carbide UDEL P1700 high-temperature plastic. By forming the window integrally with the housing, the possibility of leakage from the window during use or sterilization is greatly reduced.

The transducer chamber 226 is suitably configured to accommodate a stator assembly 234. The stator assembly 234 includes windings 236 which are machine-wound on a bobbin 235, and a magnetic core 238 constructed from transformer-type laminations or a high permesability ferrite. The magnetic poles (not shown) of the core 238 are similar to poles 40, 42 of FIG. 1 and are located at about ±45° of rotation of the rotor 212 in either direction from the center of the window 232.

The poles permit free rotation of rotor 212 between the ±45° positions. By energizing the coil 236 of the stator 234 with current of a first polarity, a magnetic field is established that causes the rotor 212 to move toward a position rotated approximately 45° from the center 243 of the window 232. By reversing the current, the rotor 212 will tend to move approximately 90° to a point approximately 45° on the other side of center of the window 232. By alternately reversing the polarity of current through the coils 236 of the stator 234, the rotor 212 can be made to oscillate in an approximately 90° arc about the center 243 of the window 232, thus defining a sector of the tissue of interest for scanning by the ultrasonic transducer 214.

The core 238 is configured with legs (not shown) similar to legs 46 and 48 of FIG. 1, the distal ends of which extend generally to the ±45° positions of rotor 212 rotation to provide the poles. The pole faces are themselves contoured in a somewhat concave manner to conform to the transverse sectional configuration of the rotor 212. The fluid coupling medium with which cavity 226 is filled coacts with the pole faces and rotor 212 to act as a snubber or shock absorber for the rotor at the endpoints of its ±45° traversals of the window 232. This promotes a smooth, shock free deceleration of the rotor 212 near these endpoints.

Lamination locator pins (not shown) locate the stator 234 lamination position accurately and prevent movement of the stator assembly 234. Alternatively, the dimensions of the cavity can be such as to prevent movement of the stator assembly 234. Flexible conductors 252 with Teflon high temperature insulation are attached to the ultrasonic transducer 214 and pass through the hollow shaft 216 and the bearing 224 into chamber 228. The magnetic axis of the permanent magnet 218 is aligned so as to pass through the transducer 214. The sonic axis of the transducer 214 can be perpendicular to the axis of the shaft 216 or may be offset by, for example, 15° to reduce reflections from the window 232.

To couple the transducer 214 output at maximum amplitude through window 232, and to couple reflections at maximum amplitude returning through window 232 back to transducer 214, cavity 226 is filled with coupling fluid 230.

The conductors 252 pass through the hollow shaft 216. These conductors are then wound in a loose "clock spring" coil 262 and positioned in the cavity 228. Stresses on the conductors 252 caused by the oscillation of the transducer 214 are thus distributed over a considerable length, leading to long flex life of the conductors 252.

The chamber 228 is closed by a housing portion 263 including a feed-through bulkhead 264 through which conductors from the stator assembly 234 and transducer 214 are coupled by conductive terminations molded into the bulkhead, while maintaining the sealed integrity of chamber 226 and chamber 228. The housing portion 263 serves as one of the retaining walls for a resilient diaphragm 266. The diaphragm 266 is clamped between the housing portion 263 and a handle support portion 268. The diaphragm 266 permits expansion and contraction of the coupling fluid in chamber 226 during use and sterilization of the system following use. The diaphragm 266 is preferably made from a high-temperature flexible material, such as a silicone. Alternatively, diaphragm 266 can be a metal bellows. The handle support portion 268 of housing 220 defines with diaphragm 266 an expansion chamber 270 which is provided with one or more vents 272 for ventilation of the interior of the chamber 270 to the exterior. The expansion chamber 270 protects the diaphragm 266 during use and sterilization.

The handle support portion 268 is provided with a shaft extension 276 which mounts a handle assembly (not shown). Shaft extension 276 is hollow to permit the conductors 252 to pass from the housing 220 to external circuitry shown in FIGS. 7–8. To prevent stress to the bulkhead connections, the conductors 252 can be glued into the shaft extension 276 using a suitable high temperature adhesive. The handle assembly can be like handle assembly 74 shown in FIG. 1.

The coupling fluid that fills chambers 226, 228 and 263 is preferably a light grade of mineral oil.

The system 210 thus provides an ultrasonic scanner that is accurate, can be hand-manipulated for insertion into a surgical cavity, and which is durable enough to withstand sterilization temperatures In the description that follows, various integrated circuit types, specific manufacturers, termminal designations and pin numbers are provided. These are only intended to be illustrative of circuit types, sources and connections of working embodiments of the invention. They are not intended to be, nor are they, representations that the circuit types, sources or connections are the only ones which can be used to practice the described invention.

Figure 7:
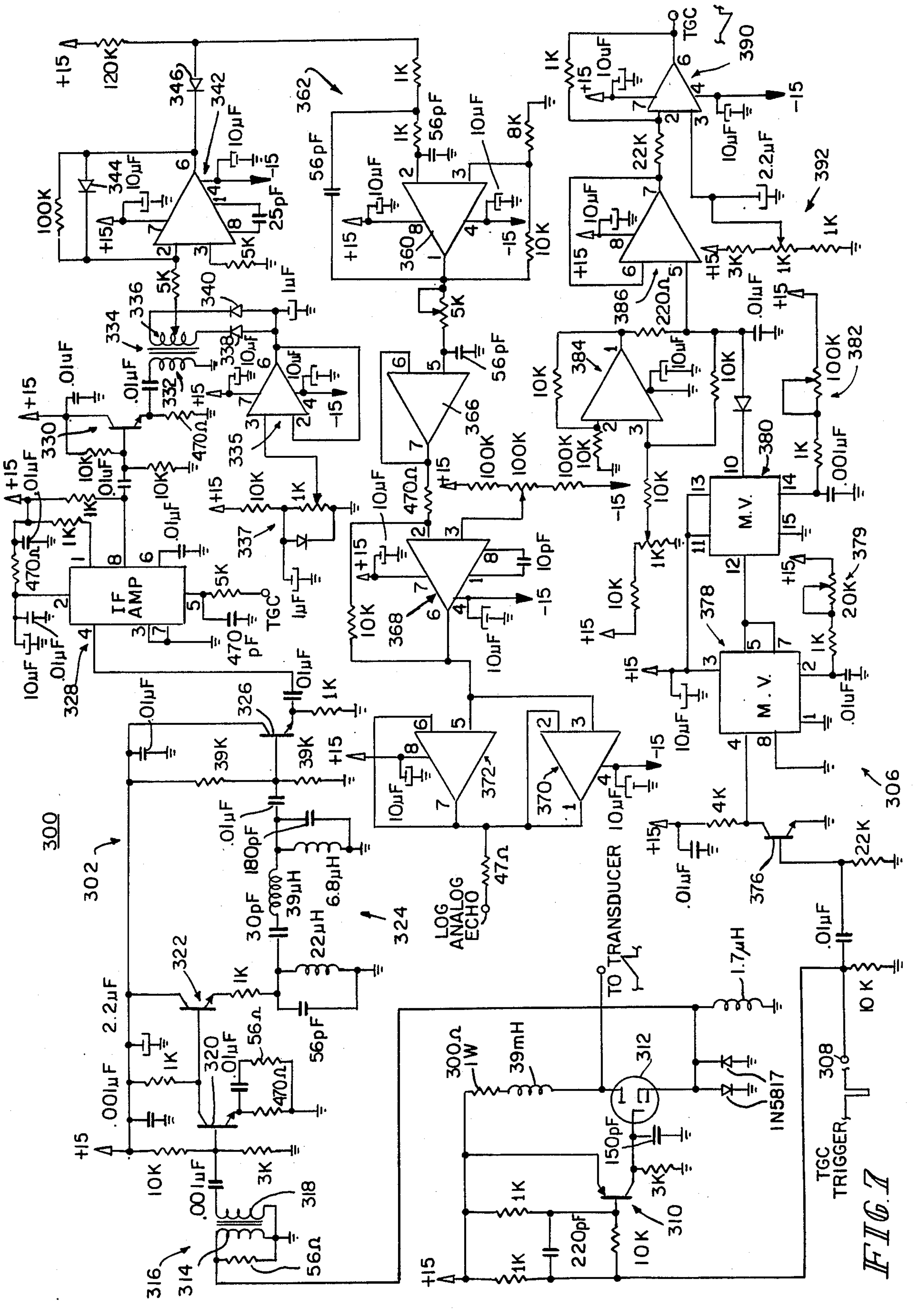
FIGS. 7, 8*a* and 8*b* illustrate, in partly block and schematic form, circuits for use with the scanners of FIGS. 3, 4 and 6.

Fig. 7 illustrates a pulse generator 300 to drive ultrasound transducer 14 (Figs. 1, 1*a*, 2), 114 (FIG. 3), 214 (FIG. 6), and a receiver and amplifier 302 for the transducer 14, 114, 214 return echoes. Receiver and amplifier 302 amplifies the signal from the transducer 14, 114, 214, generates a signal which corresponds to the logarithm of the return echo signal, rectifies the log signal, and provides a detected video output for conversion by an analog-to-digital (A/D) converter into a digital signal. This digital signal then can be processed by digital circuitry to be described in connection with FIGS. 8*a-b*.

A circuit 306 in FIG. 7 also provides time gain compensation (TGC), that is, compensation by which the gain of the amplifier 302 is adjusted as a function of time. This TGC compensates for the depth from which the echo is returning because amplitude otherwise would be lost as the echo returns from a deeper reflection site. TGC trigger input 308 responds to a negative-going input pulse. The negative-going pulse at TGC trigger 308 turns on a 2N4403 transistor 310 which turns a Siliconix IRF730 FET 312 off. While FET 312 was on, it drew a current through a 300 ohm 1W resistor and 39 mH choke from the +15 volt supply to ground. When FET 312 is turned off, the energy stored in the 39 mH choke generates a charging ramp for the transducer 14, 114 or 214. After approximately 10 microseconds, the transducer is charged to a voltage of about 150 volts across the transducer. At that time, the TGC trigger pulse at terminal 308 ends, transistor 310 again turns off, which turns FET 312 on, and shorts the transducer virtually to ground through oppositely poled IN5817 diodes. This causes a very sharp pulse in the area of 20–30 nanoseconds in width, and of negative amplitude, to be transmitted by the transducer as it rapidly discharges.

The return echoes are detected across the oppositely poled IN5817 diodes since FET 312 is on during this time, so the echoes appear across a 1.7 uH tuning choke and the primary winding 314 of a transformer 316. The secondary winding 318 of transformer 316 is coupled to the base of a 2N5179 transistor amplifier stage 320 which has a gain of approximately 15. From amplifier 320, the signal is supplied a 2N5179 emitter follower transistor stage 322 driving a filter 324. The filter 324 output signal is coupled to a 2N5179 buffer transistor stage 326. Buffer 326 drives a Motorola MC1350 integrated IF amplifier 328 with a gain control terminal (pin 5). The output terminal, pin 8 of IF amplifier 328 is coupled to the base of a 2N2222 buffer transistor stage 330 driving a primary winding 332 of a transformer 334. The secondary winding 336 of transformer 334 is split and the opposite ends of winding 336 are coupled to the cathodes of two 5082—2810 detector diodes 338, 340 to provide a full wave detector.

A type 741 operational amplifier 335 buffers a voltage generated across a bias offset circuit 337. That voltage matches the voltage drop across the diodes 338 and 340. The center tap from secondary winding 336 is coupled to an input terminal (pin 2) of an RCA CA3100 differential amplifier 342. A 1N4148 diode 344 in the feedback circuit from the output terminal (pin 6) of amplifier 342 and a 1N4148 diode 346 in the output circuit from pin 6 of amplifier 342 provide a logarithmic amplifier configuration.

The anode of diode 346 is coupled to an input terminal, pin 2, of a National Semiconductor LF353 operational amplifier 360. Operational amplifier 360 and its associated circuitry form a three pole active low pass filer 362. Filter 362 smooths the signal between its input terminal, pin 2 and its output terminal, pin 1, for later A/D conversion to be described in connection with FIGS. 8*a–b*. LF353 operational amplifier 360 is a dual operational amplifier. The other operational amplifier in the LF353 configuration forms a buffer amplifier 366. Another RCA CA3100 operational amplifier 368 coupled to the output terminal, pin 7, of operational amplifier 366 provides a gain stage with a gain of approximately 20. The output terminal, pin 6, of operational amplifier 368 is coupled to input terminals, pins 3, 5, of a National Semiconductor LF353 dual operational amplifier 370, 372 which provides a buffer amplifier for the logarithmic analog video output signal.

Turning to circuit 306, the TGC trigger pulse at terminal 308 is coupled to the base of a 2N2222 transistor input buffer stage 376. The collector of transistor 376 is coupled to an input terminal, pin 4, of a Motorola MC14538 dual monostable multivibrator integrated circuit. Transistor 376 drives the trigger for the first multivibrator 378 which provides a delay between the time that the pulse is fired by the transducer 14, 114, 214 and the time at which the TGC starts. This delay is adjustable by adjusting a 20K potentiometer 379 coupled to pin 2 of multivibrator 378. The output terminals, pins 5 and 7, of multivibrator 378 are coupled to an input terminal, pin 12, of the second multivibrator 380 in the MC14538. Multivibrator 380 and its associated circuitry, including a 100K potentiometer 382, provide a pulse of an adjustable duration after the delay established by multivibrator 378. The pulse provided at the output terminal, pin 10, of multivibrator 380 is coupled through a 1N4148 diode to an op amp 384 of a National Semiconductor LF353 dual op amp. Op amp 384 generates a negative-going ramp voltage. The other op amp 386 in the package with op amp 384 forms a buffer amplifier for the negative-going ramp voltage appearing at the output terminal, pin 1 of op amp 384. A National Semiconductor 741 op amp 390 provides attenuation and DC offset for the negative-going TGC ramp voltage. The DC offset is provided by a 1K potentiometer 392 in the circuit to an input terminal, pin 3, of op amp 390. The output terminal, pin 6, of op amp 390 is coupled to the gain control terminal, pin 5, of IF amplifier 328.

Figure 8A:
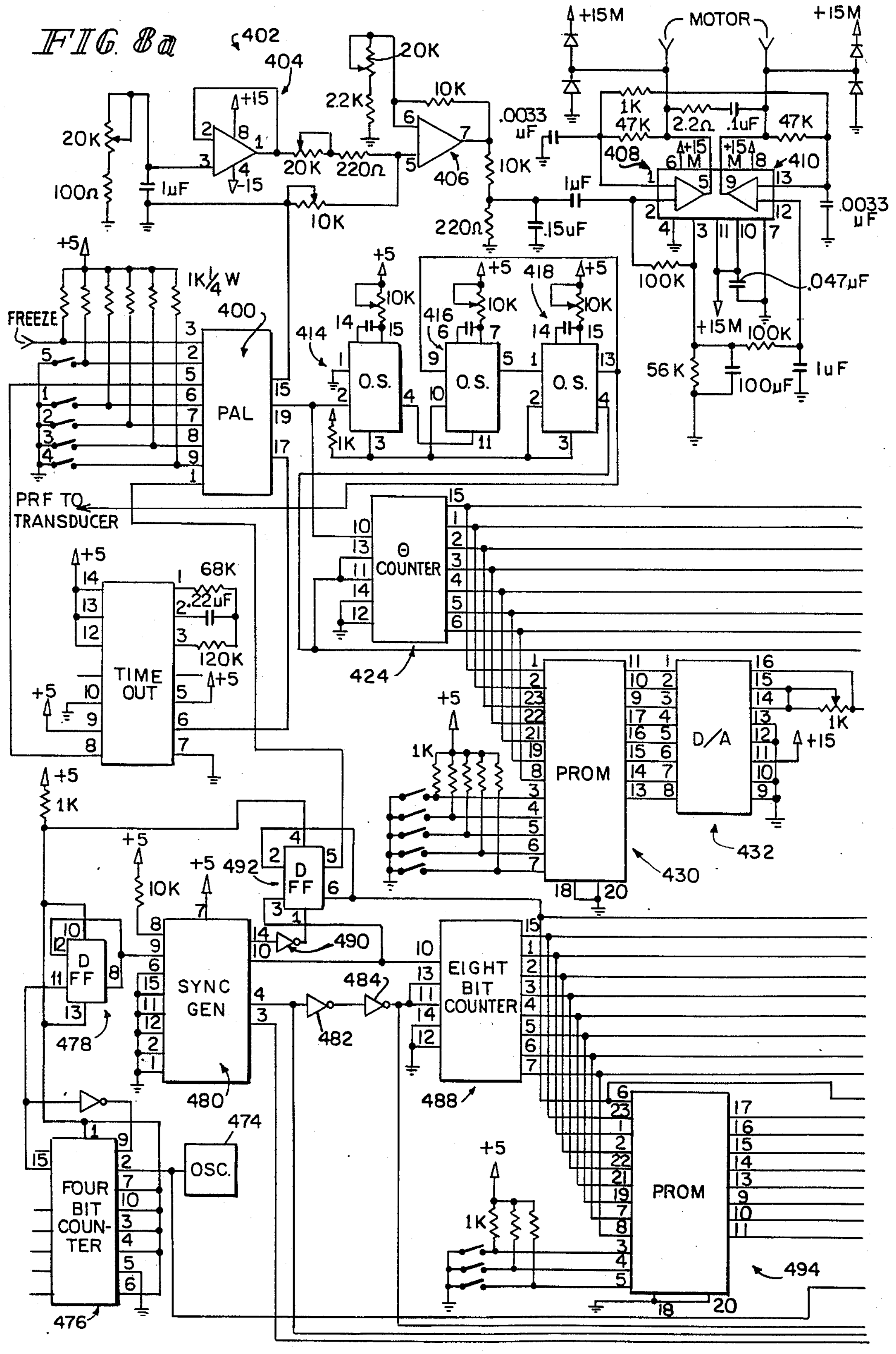
Figure 8B:
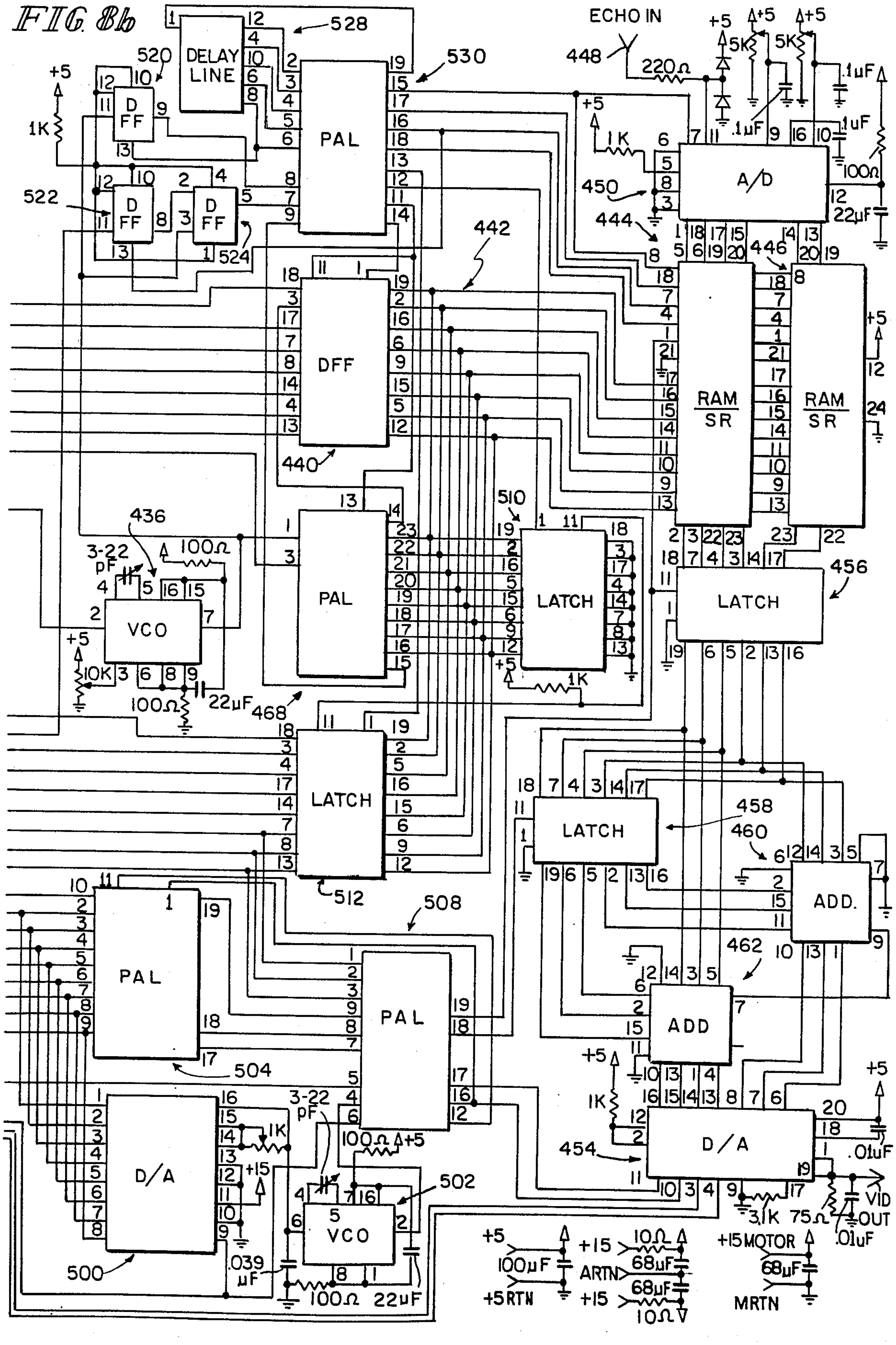

Turning to FIG. 8*b*, the power supplies for the circuits of FIGS. 7 and 8*a–b* include a +5 volt supply, +15 volt and −15 volt supplies for the analog circuits found primarily in FIG. 7, and a +15 volt motor drive.

Turning to FIG. 8*a*, a FREEZE signal comes from a switch which can be switched to ground to freeze a frame of the video display. The FREEZE signal is coupled to an input terminal, pin 3, of a Monolithic Memories Incorporated P16R8 program array logic (PAL) integrated circuit 400. PAL 400 establishes how fast the system is going to scan, that is, how many frames per second are going to update the video display. PAL 400, in effect, is a programmable counter and the FREEZE holds or overrides it. Switches 1–5 on pins 2 and 6–9 of PAL 400 establish how rapidly the display is updated. Terminal 15 of PAL 400 is coupled to an analog motor drive circuit 402.

Motor drive circuit 402 includes a National Semiconductor LM1458 dual operational amplifier. Pin 15 of PAL 400 is coupled to one terminal of a 1uF capacitor, the other terminal of which is coupled through a 20 K potentiometer and a 100 ohm resistor to ground, and to an input terminal, pin 3, of op amp 404 in the LM 1458. The output terminal, pin 1, of op amp 404 is coupled to an input terminal, pin 2, thereof, and through a 20K potentiometer and a 220 ohm resistor to an input terminal, pin 5, of an op amp 406 in the LM 1458. Pin 15 of PAL 400 is also coupled through a 10 K potentiometer to pin 5 of op amp 406.

The output terminal, pin 7, of op amp 406 is coupled through a 10 K feedback resistor to an input terminal, pin 6, thereof. Pin 6 of op amp 406 is also coupled through a 20 K potentiometer and a 2.2 K resistor to ground. Pin 7 of op amp 406 is coupled through a 10 K resistor and a 220 ohm resistor in series to ground. A 0.15 uF capacitor is coupled across the 220 ohm resistor. A 1uF, 25 volt capacitor is coupled between the junction of the 220 ohm resistor and 0.15 uF capacitor and an input terminal, pin 2, of an amplifier 408 of a Signetics TDA 1515 dual power amplifier integrated circuit.

Pin 5, the output terminal of amplifier 408, is coupled through a 47 K feedback resistor to the other input terminal, pin 1, of amplifier 408. Pin 1 is also coupled through a 0.0033 uF capacitor to ground. Pin 5 forms one of the output terminals to the motor 36 (FIGS. 1, 1*a*, 2), 136 (FIG. 3), 236 (FIG. 6) of scanner 10, 110, 210, respectively. Pin 2 of amplifier 408 is coupled through a 100 K resistor to pin 3 of the TDA1515 dual amplifier. Pin 3 is also coupled through a parallel RC circuit including a 56 K resistor and a 100 uF capacitor to ground. Pin 3 is also coupled through a 100 K resistor to an input terminal, pin 12, to an amplifier 410 of the TDA1515 dual amplifier. Pin 12 is coupled through a 1 uF capacitor to ground.

The output terminal of amplifier 410, pin 9 of the TDA1515, is coupled through a 47 K feedback resistor to the other input terminal, pin 13, of amplifier 410. Pin 9 forms the other output terminal to the motor 36, 136, 236 of scanner 10, 110, 210, respectively. Pin 13 of amplifier 410 is coupled through a 0.0033 uF capacitor to ground. Pins 5, 9 are coupled together through the series combination of a 2.2 ohm, 12 W resistor and a 0.1 uF capacitor. Pins 1 and 13 are coupled together through a 1 K resistor.

Figure 5:
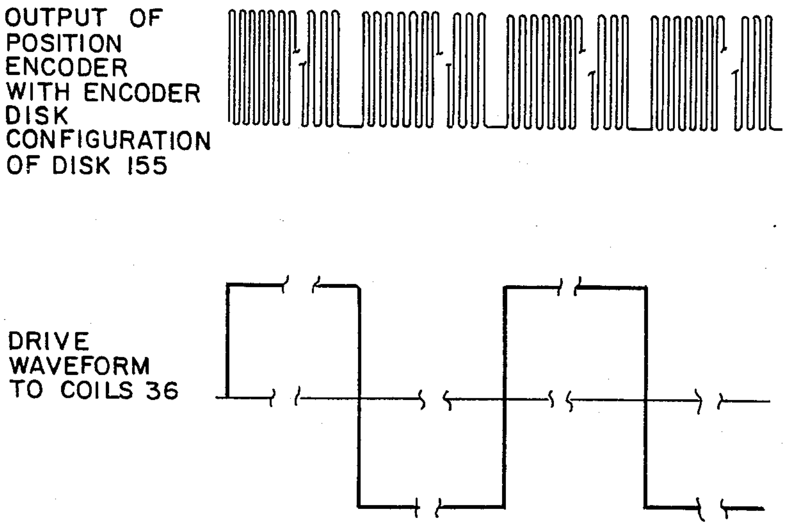
FIG. 5 illustrates a waveform which is obtained using the detail of FIG. 4 in the embodiments of FIGS. 1, 1*a*, 2 and 3.

A full wave bridge coupled between ground and the +15 volt motor supply and including four 1N4001 diodes clamps any flyback pulses appearing across the motor 36, 136, 236 terminals. Dependent on the switch setting on input terminals 2 and 6–9 to PAL 400, the motor 36, 136, 236 is driven with a number of cycles/-sec. of the drive waveform illustrated in FIG. 5, illustratively ten, to oscillate the transducer 14, 114, 214.

The video display can be thought of as a triangle with an apex to the top. There are 128 lines radiating from the apex with equal radial spacing between them. The leftmost one of these lines is the left side of the triangle. The rightmost one of these lines is the right side of the triangle. The bottom of the display is the bottom of the triangle. Once the motor 36, 136, 236 is started moving in a first direction, then the transducer 14, 114, 214 must be pulsed 128 times to generate the echo data, if there are 128 scan lines. One-shots 414, 416 and 418 control how the video display is filled with echo data. If the video display is generated at 10 frames/second, those 128 lines must be filled every 1/10 of a second. One-shots 414, 416, 418 control the speed at which the 128 lines are filled. The one-shots illustratively are TI 74LS123's, and their output at pin 13 of one-shot 418 goes to the transducer 14, 114, 214 on the PRF line.

Another output terminal, pin 4, of one-shot 418 is coupled to R> and C> inputs, pins 13 and 11 respectively, of a TI 74LS590 theta counter, or angle counter 424. The output of theta counter 424 is 8 bits of which only 7 are used, since there are only 128 scan lines. The theta counter 424 keeps the angle between the leftmost scan line of the video display (angle zero) and the current scan line of the video display by counting PRF cycles. That information is fed to an Intel 2732A PROM 430 which in turn supplies an Analog Devices AD558 D/A converter 432.

PROM 430 contains a lookup table, the values of which control a TI 74LS629 voltage controlled oscillator (VCO) 436 (FIG. 8*b*). At the leftmost and rightmost edges of the video display the frequency of VCO 436 is 0.707 MHz. At the center of the video display, the frequency of the VCO 436 is 1 MHz. Switches associated with input terminals A7–A11 (pins 3–7, respectively) of PROM 430 permit compensation for variations in the VCO 436.

Output terminals of the theta counter 424 (FIG. 8*a*) are also coupled to a TI 74LS374 octal D flip-flop 440 (FIG. 8*b*). The Q0–Q7 output terminals of the octal D flip-flop 440 are coupled through a bus 442 to the A0–A7 input terminals, pins 17–14, 11–9 and 13, respectively, of a NEC uPD41264 integrated circuit 444. Integrated circuit 444 comprises four 64K×1 RAMS. In each of the 64K×1 subsections, there is a built-in 256 ×1 shift register. If the 64K×1 subsection is though of as a 256×256 array, it will be appreciated that the uPD41264 permits the illustrated system to load one complete column of the 256 columns in the 256×256 array into the shift register and then subsequently shift it out. That transfer from the actual RAM column into the shift register takes one cycle of the RAM clock. Then the column can be shifted out to the video display. This gives the user freedom to do anything else with the RAM array because the data will already have been shifted out. In a typical RAM system, the system components are always in contention because the RAM must constantly be read to get data out to the video display. If reading from the RAM stops, the video display is lost. That takes considerable time, since RAM is being read essentially byte by byte. With the illustrated system, RAM can be read 256 times faster. This frees up the RAM for writing into it. The shift registers built into the NEC uPD41264 RAM 444 act as a sort of read/write buffer. Each NEC uPD41264 is a 4 bit device. Since the present system requires 6 bits of storage, an identical RAM 446 is coupled in parallel with RAM 444.

The digitized data for reading to and writing from the RAMS 444, 446 comes from the ECHO IN terminal 448 through an RCA CA3300 integrated circuit A/D converter 450. At the bottom of each RAM 444, 446 are serial output ports SO0–SO3. There are effectively 8 256×1 shift registers there, and they are dumped ultimately to a Telmos TML 1842 D/A converter 454, which is the video D/A converter. The output of D/A 454 at pins 1, 19 is VIDEO OUT. Between the serial output ports SO0–SO3 of RAMS 444, 446 and the video D/A converter 454 are a TI 74LS374 octal latch 456, a TI74LS374 octal latch 458, a TI 74LS283 four bit binary adder 460, and a TI 74LS283 four bit binary adder 462. Basically the data is latched into latch 456 and then the next cycle it is latched into latch 458. Adders 460 and 462 effectively form an 8-bit adder. Two values are added to obtain an average. This is done to smooth the video display. Instead of having 128 independent radiating lines from the apex of the sector displayed, the average of two adjacent lines is displayed. That smooths the display, making it look less "digital."

Returning to the write circuit including octal D flip-flop 440, the circuit also includes a Monolithic Memories Incorporated P20X10 PAL 468. Devices 440, 468 effectively supply the row and column address to the RAM 444, 446. Octal D flip-flop 440 latches in the angle (theta) value from theta counter 424 and gives a column address, and PAL 468, which is coupled as a 10 bit counter, latches a row address. When the PRF cycle starts, the counter is cleared to zero and then the counter is clocked with the VCO 436 as echo data comes in from terminal 448 through A/D 450 to RAMS 444, 446. The theta (angle or column) address and row address are incremented and supplied to the RAM 444, 446. When PAL 468 reaches 1024, it goes into a refresh mode in which it doesn't write to the RAM but provides refresh to the RAM. Since the display is 512 pixels deep from top to bottom, after 512 pixels are written to the display, then the system goes into refresh mode.

Referring to FIG. 8*a*, a Dale XO43D 25 MHz crystal oscillator 474 is coupled to a 74LS161 four bit counter 476. The output of counter 476 is coupled to a 74LS74A D flip-flop 478. A 2.045 MHz signal appears at the output terminals, pins 8 and 12, of D flip-flop 478. That signal is coupled to the D2 input terminal, pin 9, of a Ferante ZNA134J sync generator 480. Composite blanking (CBLK) on pin 4 of sync generator 480 is supplied through series inverters 482, 484 to a 74LS590 8 bit counter 488. Counter 488 generates the row address for RAM 444, 446.

The FIELD output on pin 14 of sync generator 480 is coupled through an inverter 490 to a 74LS74A D flip-flop 492. The Q output terminal of D flip-flop 492 is coupled to pin 1 of PAL 400. The $\overline{Q}$ output terminal of D flip-flop 492 and the output terminals, pins 15, 1–7, respectively, of counter 488 are coupled to the A0–A8 input terminals of an Intel 2732A PROM 494. Two functions need to be generated. One is the hold-off which is the time that the system holds off during each horizontal trace before it starts displaying the data, so that the triangle shape of the sector scan will be achieved. The hold off function basically gives the left side of the sector or triangle. The other function that must be generated is read-out rate. That will eventually establish the right side of the triangle or sector. The hold off value on the Q0–Q7 output terminals, pins 17–13, 9–11, respectively, of PROM 494 is coupled to the D0–D7 terminals of an Analog Devices AD558 D/A converter 500.

The analog output from D/A 500 controls a 74LS625 VCO 502. The hold-off value is also supplied to a Monolithic Memories Incorporated P20X10 PAL 504. PAL 504 is programmed as a 10 bit counter into which an input can be loaded. A hold-off count of from 0 to 512 is loaded into the counter 504. When the counter 504 counts up to 512, it commands the system to start displaying the data. If the video display is to be held off for a long time, such as near the top of the display, a "1" might be loaded into the counter 504 and then, 511 cycles later, counter 504 would count 512, triggering logic to start shifting data out of the RAM 444, 446. The logic that oversees this shifting includes a Monolithic Memories Incorporated P16L8 PAL 508. PAL 508 also controls the blanking to the video display through its BLK output terminal, pin 17. Q1 and $\overline{Q1}$, pins 19, 18, respectively, of PAL 508 take care of shifting data out of RAM 444, 446, and synchronizing latches 456, 458.

At the beginning of each composite blanking cycle, the system executes a data transfer cycle which moves the data from the RAM areas of RAM 444, 446 into the shift register areas of these devices. At that time, a row and column address must be provided on bus 442. The column address for the shift register effectively is always held to zero, so that, when the system starts reading the shift register, it starts with column zero and reads out. This is done by a 74LS373 octal latch 510. The row address of the row to be shifted out of the RAM 444, 446 array is provided by a 74LS373 octal latch 512. When the PRF cycle occurs, some circuitry is required to decide whether writing can occur to RAM 444, 446 or whether there is still reading and writing going on from a previous cycle. To resolve contention problems, to generate the row address strobe (RAS) and column address strobe (CAS), and to control flip-flop 440, PAL 468, and latches 510 and 512 which share the same output bus 442, circuitry including three 74LS74A D flip-flops 520, 522, 524, a Rhombus Model DTZMI-150 one hundred fifty nanoseconds max. delay line 528 and a Monolithic Memories Incorporated P16L8 PAL 530 is provided.

An RCA CD4541 timer 534 provides a twenty minute time-out signal for the drive system for the scanner. If the FREEZE feature of the scanner 10, 110, 210 is not used for 20 minutes, timer 534 deenergizes the motor windings 36, 136, 236 and the remaining circuitry to the scanner 10, 110, 210 to extend its life.

Although preferred embodiments have been described, it should be recognized that changes and modifications of the elements may be made by those skilled in the art without departing from the scope or intent of the invention.

What is claimed is:

1. A heat sterilizable ultrasonic scanner consisting essentially of a housing formed to include a fluid-receiving cavity and a vent cavity in communication with both of the fluid-receiving cavity and the atmosphere, an ultrasonic transducer enclosed within the fluid-receiving cavity of the housing, means for coupling signals between the transducer and external transducer driving circuitry and ultrasonic echo processing circuitry without fluid loss from the fluid receiving cavity, means for movably mounting the ultrasonic transducer within the housing, means for coupling signals between the means for movably mounting the transducer and external transducer moving means drive circuitry without fluid loss from the fluid receiving cavity, means for coupling ultrasonic energy from the ultrasonic transducer through the housing to a region under examination, a fluid in the fluid receiving cavity of the housing for coupling ultrasonic energy from the ultrasonic transducer to the coupling means and vice versa, and resilient diaphragm means for permitting expansion and contraction of the coupling fluid in the fluid-receiving cavity of the housing without fluid loss therefrom during use and exposure to sterilization temperatures, said diaphragm means being mounted within the housing in spaced relation to the coupling means location to form a boundary between the fluid receiving cavity and the vent cavity, the housing further including a wall defining a boundary of the vent cavity and substantially closing the vent cavity, the wall being formed to include an aperture interconnecting the vent cavity and the atmosphere, the wall protecting the resilient diaphragm means during sterilization and use while permitting air contained in the vent cavity to be discharged to the atmosphere via the aperture in response to movement of the resilient diaphragm means during expansion of the coupling fluid in the fluid-receiving cavity.

2. The scanner of claim 1 wherein the means for movably mounting the ultrasonic transducer includes an armature for supporting the transducer for movement therewith.

3. The scanner of claim 2 wherein the means for movably mounting said ultrasonic transducer further comprises a permanent magnet mounted on said armature, and a stator mounted within said housing.

4. The scanner of claim 3 wherein the stator includes means for limiting the movement of the transducer within the housing.

5. The scanner of claim 4 wherein the means for limiting the movement of the transducer within the housing includes means formed at the ends of the stator defining approximately the outer limits of armature rotation.

6. The scanner of claim 1, wherein the resilient diaphragm means has a first cross-sectional area and the aperture has a second cross-sectional area substantially smaller than the first cross-sectional area.

7. A heat sterilizable ultrasonic scanner consisting essentially of an ultrasonic transducer, rotor means for rotatably mounting the ultrasonic transducer for movement along an arcuate path, stator means for imparting rotational motion to the rotor means to move the ultrasonic transducer along the arcuate path, a housing formed to include a liquid-receiving cavity enclosing the ultrasonic transducer, the rotor means, and the stator means, and a vent cavity communicating with the liquid-receiving cavity and the atmosphere, the housing including acoustically transparent means for transmitting ultrasonic energy from and to the liquid-receiving cavity, a coupling liquid in the liquid-receiving cavity for conducting ultrasonic energy from and to the ultrasonic transducer, resilient diaphragm means forming a boundary of the liquid receiving cavity for permitting expansion and contraction of the volume of the liquid receiving cavity to permit expansion and contraction of the coupling fluid without fluid loss from the liquid receiving cavity during use and exposure to sterilization temperatures, the resilient diaphragm means forming the interface between the liquid-receiving cavity and the vent cavity, the resilient diaphragm means being spaced from the acoustically transparent means, the housing further including wall means for substantially covering the resilient diaphragm means, the wall means forming the interface between the vent cavity and the atmosphere and including an aperture interconnecting the vent cavity and the atmosphere, the wall means protecting the resilient diaphragm means during use and sterilization while permitting air contained in the vent cavity to be discharged to the atmosphere via the aperture in response to movement of the resilient diaphragm means during expansion of the coupling fluid in the liquid-receiving cavity and permitting air from the atmosphere to enter the vent cavity via the aperture in response to movement of the resilient diaphragm means during contraction of the coupling fluid in the liquid receiving cavity and means for coupling signals between the transducer and external transducer driving circuitry and ultrasonic echo processing circuitry without liquid loss from the liquid-receiving cavity and for coupling signals between the stator means and external stator means drive circuitry without liquid loss from the liquid-receiving cavity.

8. The scanner of claim 7, wherein the acoustically transparent means comprises a rigid housing portion.

9. The scanner of claim 7, wherein the rotor means includes an elongated armature, the ultrasonic transducer being fixed to one end of the armature, and a shaft for rotatably supporting the armature within the housing so that the ultrasonic transducer sweeps along the arcuate path during rotation of the armature.

10. The scanner of claim 9, wherein the rotor means includes a permanent magnet fixed to the other end of the elongated armature, and the stator means includes a magnetic core assembly for conducting a magnetic field established by energizing the core assembly with an electrical current from the external stator means drive circuitry, the stator means drive circuitry including means for applying an electrical current to the magnetic core assembly and, for changing the polarity of the energizing electrical current to vary the magnetic field of the stator means such that the armature oscillates under the control of the field.

11. The scanner of claim 7, wherein the stator means defines stop means for limiting movement of the rotor means along the arcuate path.

12. The scanner of claim 7, wherein the resilient diaphragm means has a first cross-sectional area and the aperture has a second cross-sectional area substantially smaller than the first cross-sectional area.

* * * * *